US006251413B1

(12) United States Patent
Ferrari et al.

(10) Patent No.: US 6,251,413 B1
(45) Date of Patent: Jun. 26, 2001

(54) AQUEOUS COSMETIC COMPOSITION COMPRISING A SULFONATED POLYESTER AND A SILICONE COMPOUND

(75) Inventors: Véronique Ferrari, Maisons-Alfort; Valérie de la Poterie, Le Chatelet en Brie, both of (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/388,558

(22) Filed: Sep. 2, 1999

(30) Foreign Application Priority Data

Sep. 14, 1998 (FR) .................................. 98 11433

(51) Int. Cl.$^7$ ............................ A61K 7/00; A61K 31/74; A61K 33/04
(52) U.S. Cl. .................. 424/401; 424/78.07; 424/78.08; 424/400; 424/703; 424/DIG. 5
(58) Field of Search ................................ 424/400, 401, 424/78.02, 78.08, 703, DIG. 5

(56) References Cited

U.S. PATENT DOCUMENTS

| 3,779,993 | 12/1973 | Kibler et al. . |
| 4,300,580 | 11/1981 | O'Neill et al. . |
| 5,260,052 | 11/1993 | Peters et al. . |
| 5,389,363 | 2/1995 | Snyder et al. . |
| 5,866,111 | 2/1999 | Felardos et al. . |

FOREIGN PATENT DOCUMENTS

| 2 742 986 | 7/1997 | (FR) . |
| 2 760 636 | 9/1998 | (FR) . |
| 2 760 642 | 9/1998 | (FR) . |
| 2 238 242 | 5/1991 | (GB) . |
| WO 94/15580 | 7/1994 | (WO) . |
| WO 95/32997 | 12/1995 | (WO) . |
| WO 96/33689 | 10/1996 | (WO) . |
| WO 97/24102 | 7/1997 | (WO) . |
| WO 97/45094 | 12/1997 | (WO) . |

OTHER PUBLICATIONS

English language Derwent Abstract of EP 0 775 483, May 28, 1997.
English language Derwent Abstract of EP 0 811 372, Dec. 10. 1997.
English language Derwent Abstract of EP 0 864 319, Sep. 16, 1998.
English language Derwent Abstract of EP 0 865 786, Sep. 23, 1998.
English language Derwent Abstract of FR 2 688 134, Sep. 10, 1993.
English language Derwent Abstract of FR 2 742 986, Jul. 4, 1997.
English language Derwent Abstract of FR 2 760 636, Sep. 18, 1998.
English language Derwent Abstract of FR 2 760 642, Sep. 18, 1998.
Charles Todd et al., "Volatile Silicone Fluids for Cosmetic Formulations", Cosmetics and Toiletries, vol. 19, Jan. 1976, pp. 29–32.

*Primary Examiner*—Shelley A. Dodson
(74) *Attorney, Agent, or Firm*—Finnegan Henderson Farabow Garrett & Dunner, L.L.P.

(57) ABSTRACT

A cosmetic or dermatological composition comprising, in an aqueous phase:
i) a water-soluble or water-dispersible terephthalic copolyester oligomer comprising dicarboxylate repeat units of formula (I):

$$[-CO-A-CO-O-(CH_2-CH_2O)_n-] \tag{I}$$

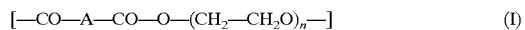

wherein
  A is 1,4-phenylene and sulfo-1,3-phenylene groups,
  n ranges from 1 to 4,
  at least 35 mol % of said units of formula (I) are units of formula (I), wherein A is a 1,4-phenylene group and n is equal to 1,
  at least 7 mol % of said units of formula (I) are units of formula (I), wherein A is a sulfo-1,3-phenylene group, and
  the weight-average molecular mass of said copolyester oligomer is less than 20,000, and
ii) at least one silicone compound as an emulsion in the aqueous phase, and the composition is intended for making up keratinous substances.

35 Claims, No Drawings

AQUEOUS COSMETIC COMPOSITION COMPRISING A SULFONATED POLYESTER AND A SILICONE COMPOUND

The present invention relates to a novel water-resistant, transfer resistant, preferably transfer free, film-forming composition for topical application, comprising a specific hydrophilic gelling agent of sulfonated polyester type and a silicone compound, intended in particular for the cosmetics and/or dermatological fields. The invention also relates to the use of this composition for making up or cosmetically treating human keratinous substances, such as the skin, nails, eyelashes, eyebrows, hair or mucous membranes, such as the lips. This composition can be provided in the form of a gel, paste or cast product, in particular a stick.

Products for making up or caring for the skin or lips, such as foundations or lipsticks, generally comprise fatty phases, such as waxes and oils, pigments and/or fillers and, optionally, additives, such as cosmetic or dermatological active principles. They can comprise gelling agents which make it possible to obtain the consistency desired for the composition according to its application.

These compositions, when they are applied to the skin or lips, exhibit the disadvantage of transferring, that is to say of being at least partly deposited, while leaving traces on certain substrates with which they can be brought into contact, in particular a glass, a cup, a cigarette, an item of clothing or the skin. This results in mediocre persistence of the applied film, requiring the regular renewal of the application of the foundation or lipstick composition. In addition, the appearance of these unacceptable traces, in particular on blouse collars, can dissuade some women from using this type of make-up.

So-called transfer resistant make-up compositions comprising volatile oils, in particular volatile silicone oils and/or volatile hydrocarbon-comprising oils, are known from Applications EP-A-602,905 and JP-A-6165809. However, these compositions can be uncomfortable to wear (feeling of tautness and of drying out), in particular on the lips, and can result in a matt make-up.

Compositions for the lips comprising an aqueous polymer dispersion have also been provided in Application EP-A-775,483. Although these compositions result in films having good transfer resistant properties, these films unfortunately can have the disadvantage of being uncomfortable over time. Furthermore, these films can be difficult to remove with commonly used make-up removers.

The aim of the present invention is to provide an aqueous film-forming composition which does not exhibit the disadvantages mentioned above and which exhibits, in particular, properties of excellent resistance from transfer, if not total freedom from transfer, of gloss, of decreased if not absence of tautness during and after application to keratinous substances, and of ease of removal.

The inventors have discovered that such a composition can be obtained by using a specific hydrophilic gelling agent of sulfonated polyester type and at least one silicone compound in aqueous emulsion. A composition is then obtained which leaves, after application, a film which can exhibit good gloss and good hold and which can exhibit excellent resistance to, if not complete freedom from, transfer. The film can be nonsticky and comfortable (nontautening) during and after application of the composition to keratinous substances. The film can also produce a feeling of freshness and can be easy to remove with commonly used make-up removers. Furthermore, the composition can be easily applied to keratinous substances.

A film-forming composition comprising a sulfonated terephthalic copolyester oligomer and 2% by weight of an aminosilicone in aqueous emulsion is known in Application FR-A-2,760,642, published on Sep. 18, 1998.

The subject-matter of the present invention is therefore a novel film-forming composition for topical application comprising, in an aqueous phase, a hydrophilic gelling agent of sulfonated polyester type, characterized in that the hydrophilic gelling agent is a water-soluble or water-dispersible terephthalic copolyester oligomer and in that the composition also comprises at least one silicone compound as an emulsion in the aqueous phase.

The specific gelling agents used according to the invention are water-soluble or water-dispersible terephthalic copolyester oligomers comprising dicarboxylate repeat units of formula (I):

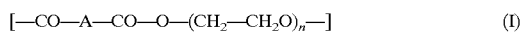

$$[-CO-A-CO-O-(CH_2-CH_2O)_n-] \quad (I)$$

wherein
  A is chosen from 1,4-phenylene and sulfo-1,3-phenylene groups and optionally 1,3-phenylene groups,
  n ranges from 1 to 4,
  at least 35 mol % of the said units of formula (I) are units of formula (I), in which A represents a 1,4-phenylene group and n is equal to 1,
  at least 7 mol % of the said units of formula (I) are units of formula (I), in which A represents a sulfo-1,3-phenylene group, and
  the weight-average molecular mass of the said copolyester oligomers is preferably less than 20,000, and more preferably less than 15,000.

Preferably, at least 40 mol % and more preferably between 40 and 90 mol %, inclusive, of the units of formula (I) are units of formula (I), in which A represents a 1,4-phenylene group and n is equal to 1. Preferably, at least 10 mol %, and more preferably between 10 mol % and 25 mol %, inclusive, of the units of formula (I) are units of formula (I), wherein A is a sulfo-1,3-phenylene group.

The ends of the chains of the said copolyester oligomers can be alike or different and comprise groups of formula (I'):

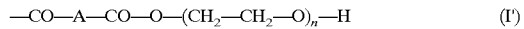

$$-CO-A-CO-O-(CH_2-CH_2-O)_n-H \quad (I')$$

in which A and n are defined above.

The said oligomers can also comprise at the chain ends, in a minor amount, groups of formulae

$$-A-CO-OH$$

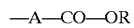

$$-A-CO-OR$$

in which formulae A is defined above and R represents a $C_1$–$C_4$ alkyl group.

When A represents a sulfo-1,3-phenylene group, it is preferably an alkali metal, in particular sodium or potassium, sulfonate or an ammonium or mono-, di-, tri- or tetra(lower alkyl)ammonium sulfonate. The term "(lower alkyl)ammonium" is preferably understood to mean an ammonium, the alkyl radical or radicals of which are lower alkyls, preferably $C_1$–$C_6$ alkyls. Sodium sulfonate is preferred.

The copolyester oligomer can optionally comprise up to 20 mol %, preferably from 0.5 to 5 mol %, of units of formula (I) in which A represents a 1,3-phenylene group.

According to a preferred embodiment of the invention, the above copolyester oligomer has a weight-average molecular mass ranging from 5000 to 14,000 and more preferably from 8000 to 10,000. The weight-average molecular masses are measured by gel permeation chromatography in dimethylacetamide comprising $10^{-2}$N of LiBr at 100° C. The results are expressed in polystyrene equivalents.

The said copolyester oligomers can be obtained by standard processes for the preparation of polyesters by the molten route, solvent route or interfacial route, which processes comprise esterification reactions of diacids and of diols and polycondensation reactions, transesterification reactions of diesters and of diols and polycondensation reactions, self-condensation reactions of hydroxy acids, Schotten-Baumann reactions, by employing diols and acid chlorides, and polycondensation reactions, and polymerization reactions of lactones.

The minimum content of units of formula (I) in which A represents a 1,4-phenylene group and n is equal to 1 is controlled, both by the initial stoichiometric ratios of the various monomers and by controlling the side reactions.

A particularly advantageous method of preparation comprises transesterification/polycondensation and/or esterification/polycondensation by the molten route using a transesterification and/or esterification catalyst.

The structure is controlled by controlling the minimum content of units of formula (I) in which A represents a 1,4-phenylene group and n is equal to 1, both by the initial stoichiometric ratios of the various diacid and/or diester and diol monomers and by employing an etherification-limiting agent, which limiting agent can be a basic compound, such as aliphatic or aromatic amines or an alkali metal or alkaline earth metal hydroxide or acetate.

The molecular mass is controlled in a way known to a person skilled in the art, by an appropriate compromise between the pressure, the temperature and the time.

The terephthalic copolyester oligomers used according to the invention can be prepared by esterification and/or transesterification/polycondensation of a monomer composition based:

on terephthalic acid, anhydride or diester (Tp)

on sulfoisophthalic acid, anhydride or diester (Slp)

optionally on isophthalic acid, anhydride or diester (Ip) and on ethylene glycol (EG)

according to relative amounts corresponding to an (Slp)/[(Tp)+(Slp)+(Ip)] molar ratio of at least 7/100, preferably of at least 10/100, very particularly of 10/100 to 25/100 an (Ip)/[(Tp)+(Slp)+(Ip)] molar ratio of 20/100 at most, preferably of 5/100 at most an (EG)/[(Tp)+(Slp)+(Ip)] molar ratio of 2/1 to 3/1, in the presence of an esterification and/or transesterification catalyst and of an etherification-limiting agent.

The terephthalic monomer (Tp) is preferably employed in the form of a lower diester ($C_1$–$C_4$ dialkyl diester), preferably the dimethyl diester. The sulfoisophthalic monomer (Slp) is preferably employed in the form of an alkali metal (in particular sodium) sulfonate of a lower ($C_1$–$C_4$ alkyl) diester, preferably the methyl diester. Mention may very particularly be made of dimethyl 5-(sodiooxysulfonyl) isophthalate. The optional isophthalic monomer (Ip) is preferably employed in the form of isophthalic acid.

When all the "diacid" monomers are employed in the form of diesters, the transesterification (interexchange) operation between these "diacid" monomers and the ethylene glycol is generally carried out at a temperature greater than or equal to 130° C., preferably from about 140 to about 220° C., and very particularly from about 180 to about 220° C.; at this temperature, the methanol (preferred case of the methyl diesters) formed is removed from the reaction mixture, preferably by distillation.

This interexchange operation is carried out in the presence of a metal transesterification catalyst and of an etherification-limiting agent. The said catalyst is preferably a metal carboxylate, such as manganese acetate, zinc acetate, cobalt acetate or calcium acetate, or an organic or inorganic titanate, such as butyl titanate, 2,2',2"-nitrilotriethyl titanate (or titanium aminotriethanolate, additionally acting as etherification-limiting agent) or calcium titanate. The preferred catalysts are organic titanates; they are employed in amounts of from about 0.001% by weight, expressed as titanium, preferably from about 0.002% to about 0.02% by weight of titanium, with respect to the weight of reactants present.

The etherification-limiting agent can be a basic compound, such as aliphatic or aromatic amines (triethanolamine, guanidine carbonate, dimethylaniline, naphthylamine, and the like) or an alkali metal or alkaline earth metal hydroxide or acetate (sodium acetate, potassium acetate, sodium benzoate, and the like). It is generally employed in an amount of from about 0.001% to about 0.05% with respect to the weight of reactants present.

The duration of the interexchange operation is generally from 1 to 4 hours; it is preferably from about 2 to about 3 hours.

When more than 90% of the theoretical amount of methanol has been distilled off, the excess polyol is removed by bringing the temperature of the reaction mixture to 230° C.

The polycondensation operation is preferably carried out at a temperature of from about 230 to about 280° C., more preferably from about 240 to about 260° C., in another reactor brought beforehand to this temperature and gradually placed under vacuum down to a pressure which can range down to 10 Pa; a reduction in pressure down to approximately 10 millibar lasts about 40 minutes.

The polycondensation operation takes place with removal of polyol molecules; this operation is stopped when the motor torque of the stirrer shaft shows a value equivalent to approximately 0.5 to 5 newton meters for a temperature of the reaction mass of 250° C. and a stirrer speed of 80 revolutions/minute of an anchor-shaped stirrer in a 7.5 liter reactor. The vacuum is subsequently broken with nitrogen and the polymer is cast in a mould; after cooling, the polymer is milled.

When one of the "diacid" monomers is present in the diacid or anhydride form and the other or others in the diester form, said copolyester oligomers are obtained by first carrying out a transesterification operation on the diester monomers with ethylene glycol under the conditions described above, followed by an esterification operation in the medium on the diacid or anhydride monomer with ethylene glycol and then polycondensation under the conditions described above, the total amount of ethylene glycol being divided between the two operations (transesterification and esterification).

If necessary, the esterification operation is carried out by addition, to the reaction mixture resulting from the transesterification operation, of the monomer in the diacid or anhydride form and of ethylene glycol, suspended beforehand, at a temperature corresponding to that of the end of the interexchange temperature: the introduction period is generally of the order of 1 hour.

This esterification operation is generally carried out at a temperature of from about 230 to about 280° C., preferably from about 250 to about 260° C., in the presence of a catalyst of the same type as that for transesterification and of an etherification-limiting agent. The operation is carried out in the presence of the same types of catalyst and of etherification-limiting agent as those employed during the transesterification operation, in the same proportions. The reaction is carried out with removal of water, which is withdrawn from the reactor at the same time as the excess polyol. This type of preparation process is disclosed in particular in Patent Application WO 95/32997, the disclosure of which is specifically incorporated by reference herein.

In general, the terephthalic copolyester oligomer can be present in the composition according to the invention in a content ranging from 0.5% to 40% by weight with respect to the total weight of the composition. Different amounts of specific gelling agent will be employed according to the desired form, gelled, pasty or solid. For a solid composition, use will preferably be made of 10 to 40% by weight of specific gelling agent, more preferably of 15 to 30% by weight. For a gelled or pasty composition, use will preferably be made of 0.5 to 10% by weight of specific gelling agent, more preferably of 2 to 5% by weight.

The at least one silicone compound present in the composition according to the invention is in the form of an aqueous emulsion, also known as a silicone emulsion.

The term "aqueous emulsion" is understood to mean an emulsion of oil-in-water type in which the silicone compound is dispersed in the form of particles or droplets in the aqueous phase forming the continuous phase of the emulsion. This emulsion can be stabilized by a conventional emulsifying system.

This silicone emulsion can have a size of silicone droplets or particles ranging from 10 nm to 50 $\mu$m and preferably from 10 nm to 1000 nm. It can also be provided in the form of a microemulsion having a size of silicone droplets of the order of 10 to 80 nm. Silicone microemulsions are stable emulsions of colloidal particles and are generally transparent.

The silicone compounds, in emulsion, are preferably polyorganosiloxanes, which can be provided in the form of oils, in particular of volatile or nonvolatile silicone oil, of gums, of resins, of pasty products or of waxes, or their mixtures.

These silicone compounds are generally easily emulsifiable in an aqueous medium using surfactants commonly employed with these silicone compounds, such as the (alkyl) dimethicone copolyols or the surfactants cited in the document EP-A-678,015, the disclosure of which is specifically incorporated by reference herein.

The silicone gums, waxes and resins can be mixed with silicone oils in which they may be dissolved, the mixture being in the form of an emulsion in the aqueous phase of the composition according to the invention.

Generally, the silicone compounds are polymers comprising repeat units of formula (II): $R_nSiO_{(4-2)/2}$ The R substituents present in these repeat units are organic groups and can be identical or different. In addition, the same compound can comprise different repeat units.

The repeat units corresponding to n=2 correspond to a compound having a linear or cyclic structure, the chain of which comprises siloxane bonds. In the case of a linear polymer, units corresponding to n=3 constitute the end groups.

In addition, the silicone compounds can comprise crosslinking units inserted between the repeat units. These crosslinking units correspond to the above formula (II) with n=1 or n=0.

The repeat units in which n=4 correspond to a crosslinked polymer, the end groups of which can be units in which n=1, 2 or 3.

The R groups of the formula (II) can represent in particular alkyl, alkenyl, cycloalkyl, aryl, alkylaryl or hydroxyl groups and can additionally comprise functional groups, such as ethers, amines, carboxyls, hydroxyls, thiols, esters, sulfonates or sulfates.

The alkyl groups have, for example, 1 to 50 carbon atoms; the cycloalkyl groups have, for example, 5 or 6 carbon atoms; the aryl groups are in particular phenyl groups; the alkenyl groups have in particular from 2 to 10 carbon atoms; and the alkylaryl groups can generally have from 7 to 20 carbon atoms.

In the case of the end groups corresponding to n=3, one of the R groups attached to the end silicon can additionally comprise another group, such as an OH group.

Mention may be made, among the silicone compounds capable of being used in the composition of the present invention, of nonvolatile silicones, chosen in particular from polyorganosiloxanes and especially polyalkylsiloxanes, polyarylsiloxanes, polyalkylarylsiloxanes, polyethersiloxane copolymers, which may or may not be organomodified, silicone gums, pasty products, waxes and resins, polysiloxanes modified by organofunctional groups, and their mixtures.

They are chosen more particularly from polyalkylsiloxanes, among which may mainly be mentioned linear polydimethylsiloxanes with trimethylsilyl end groups having a viscosity of $10^{-5}$ to 2.5 m²/s at 25° C., preferably of 1×10–5 1 m²/s at 25° C., and in particular the following commercial products:

Silbione oils of the 47 and 70047 series sold by Rhône-Poulenc, such as, for example, the 47V500000 oil, oils of the 200 series from Dow Corning, Viscasil oils from General Electric, and certain oils of the SF series (SF96, SF18) from General Electric.

Mention may also be made of linear polydimethylsiloxanes with dimethylsilanol end groups, such as the oils of the 48 series from Rhône-Poulenc.

Mention may also be made of the products sold under the names Abil Wax 9800 and 9801 by the company Goldschmidt, which are poly($C_1$–$C_{20}$)alkylsiloxanes.

Mention may be made, among polyalkylarylsiloxanes, of linear or branched polydimethylmethylphenylsiloxanes and polydimethyidiphenylsiloxanes having a viscosity of 1×$10^{-5}$ to 5×$10^{-2}$ m²/s at 25° C. and in particular the following commercial products:

Silbione oils of the 70641 or 70633 V 30 series from Rhône-Poulenc, oils of the Rhodorsil 70633 and 763 series from Rhône-Poulenc, DC 556 Fluid or SF 558 oil from Dow Corning, silicones of the PK series from Bayer, such as the product PK20, silicones of the PN and PH series from Bayer, such as the products PN1000 and PH1000, certain oils of the SF series from General Electric, such as SF1023, SF1154, SF1250 and SF1265, and Abil AV 8853 oils from Goldschmidt.

The silicone gums which can be used according to the present invention are in particular polydiorganosiloxanes having high molecular masses, preferably of between 200,000 and 1,000,000, inclusive. They can be used alone or as a mixture in a solvent which can be chosen from volatile silicones, polydimethylsiloxane (PDMS) oils, polyphenylmethylsiloxane (PPMS) oils, isoparaffins, methylene chloride, pentane, dodecane, tridecane, tetradecane or their mixtures.

Mention may more particularly be made of the following products:

polydimethylsiloxane/methylvinylsiloxane,
—polydimethylsiloxane/diphenylsiloxane,
—polydimethylsiloxane/phenylmethylsiloxane, or
—polydimethylsiloxane/diphenylsiloxane/methylvinylsiloxane gums.

Use may in particular be made of mixtures such as:

the mixtures formed from a polydimethylsiloxane hydroxylated at the chain end (dimethiconol according to the CTFA) and from a cyclic polydimethylsiloxane (cyclomethicone according to the CTFA), such as the product Q2-1401 sold by the company Dow Corning, the mixtures formed from a polydimethylsiloxane gum with a cyclic silicone oil, such as the product SF1214 from General Electric (which is a mixture of dimethicone gum, having a molecular weight of 500,000, dissolved in decamethylcyclopentasiloxane), the mixtures of two PDMSs with different viscosities, in particular of a PDMS gum and of a PDMS oil, such as the product SF1236 from the company General Electric (which is a mixture of 15% of dimethicone gum having a molecular weight of 500,000, with a viscosity of 20 $m^2/s$, and of 85% of SF96 oil with a viscosity of $5 \times 10^{-6}$ $m^2/s$).

Mention may be made, as silicone waxes, of those disclosed in the documents FR-A-2,688,134 and EP-A-811, 372, the disclosures of which are specifically incorporated by reference herein.

The organopolysiloxane resins which can be used according to the invention are in particular crosslinked siloxane systems including the $R_2SiO$, $RSiO_{3/2}$ and $SiO_2$ units. The more particularly preferred products among these compounds are those in which R denotes a $C_1$–$C_{36}$ alkyl or phenyl.

Mention may be made, among these resins, of the product sold under the name Dow Corning 593 or those sold under the names Silicone Fluid SS4230 and SS4267 by the company General Electric, which are of dimethyl/trimethylsiloxane type.

The organomodified silicones are silicone compounds as defined above additionally comprising, in their structure, one or more organofunctional groups directly attached to the siloxane chain or attached via a hydrocarbon-comprising radical.

Mention may be made, for example, of the silicones comprising:

polyethyleneoxy and/or polypropyleneoxy groups optionally comprising alkyl groups, such as:
dimethicone copolyols and in particular that sold by the company Dow Corning under the name DC1248,
alkyl (di)methicone copolyols and in particular the ($C_{12}$)alkyl methicone copolyol sold by the company Dow Corning under the name Q2-5200,
Silwet L 722, L 7500, L 77 and L 711 oils from the company Union Carbide, optionally substituted amino groups, such as the products sold under the name GP4 Silicone Fluid and GP7100 by the company Genesee or the products sold under the names Q2-8220 and DC929 by the company Dow Corning, wherein the substituted amino groups are in particular ($C_1$–$C_4$)alkylamino groups, thiol groups, such as GP 72 A and GP 71 from Genesee,
carboxylate groups, such as the products disclosed in Patent EP 186,507, the disclosure of which is specifically incorporated herein by reference, from the company Chisso Corporation,
alkoxylated groups, such as the products sold under the name Silicone copolymer F-755 by SWS Silicones or Abil Wax 2428, 2434 and 2440 by the company Goldschmidt,
hydroxylated groups, such as the polyorganosiloxanes with a hydroxyalkyl functional group disclosed in particular in French Patent Application 85FR-16334, the disclosure of which is specifically incorporated herein by reference,
acyloxyalkyl groups, such as, for example, the polyorganosiloxanes disclosed in French Patent Application 88FR-17433, the disclosure of which is specifically incorporated herein by reference, wherein these compounds can be prepared by esterification of polyorganosiloxanes with a hydroxyalkyl functional group,
anionic groups of carboxyl type, such as alkylcarboxyl groups, 2-hydroxyalkylsulfonate or 2-hydroxyalkylthiosulfate, and
fluorinated groups.

Mention may also be made, among the silicone compounds capable of being used in the composition according to the invention, of volatile silicones which generally have a boiling point of between 60° C. and 260° C., inclusive, and a viscosity of less than $10^{-5}$ $m^2/s$ and in particular:

cyclic silicones comprising from 3 to 7 silicon atoms and preferably 4 to 6 silicon atoms, such as octamethylcyclotetrasiloxane, decamethylcyclopentasiloxane and their mixtures.

Mention may also be made of cyclocopolymers, such as dimethylsiloxane/methylalkylsiloxane, and in particular the volatile silicone FZ 3109 sold by the company Union Carbide.

Mention may also be made of the mixtures of cyclic silicones with compounds derived from silicon, such as the (50/50) mixture of octamethylcyclotetrasiloxane and of tetra (trimethylsilyl)pentaerythritol and the mixture of octamethylcyclotetrasiloxane and of 1,1'-oxy(2,2,2',2',3,3'-hexatrimethylsilyloxy)bisneopentane.

volatile linear silicones comprising 2 to 10 carbon atoms and a viscosity of less than or equal to $10^{-5}$ $m^2/s$ at 25° C., such as polydimethylsiloxanes (PDMS), for example hexamethyldisiloxane, decamethyltetrasiloxane or dodecamethylcyclohexasiloxane and those cited in the document EP-A-811,372, the disclosure of which is specifically incorporated herein by reference. Silicones coming within this class are also described in the article published in Cosmetics and Toiletries, vol. 91, January 1976, pp. 27–32, entitled "Volatile Silicone Fluids for Cosmetics", the disclosure of which is specifically incorporated herein by reference.

The aqueous emulsion of silicone compounds can easily be prepared by a person skilled in the art on the basis of his overall knowledge.

Mention may be made, among commercially available aqueous silicone emulsions, of:

polydimethylsiloxane emulsions (SM2162 from General Electric),
stearyl dimethicone emulsions (SLM23032 from Wacker),
amodimethicone microemulsions (Microemulsion 71827 from Rhône-Poulenc), cationic microemulsions of polydimethylsiloxane with aminoethylaminopropyl groups (DC939 from Dow Corning), polydimethylsiloxane microemulsions (Siltech MFF 5015-70 from Siltech or DC2-1281 from Dow Corning), cationic emulsions of aminated polydimethylsiloxanes (Belsil ADM 6057 E from Wacker), phenylated polydimethylsiloxane emulsions (Mirasil DPDM-E from Rhône-Poulenc), and alkylated polydimethylsiloxane emulsions (Silres M50E from Wacker).

The silicone compounds can be present in the composition in a proportion of 0.1% to 30% by weight on a dry basis of silicone compound with respect to the total weight of the composition and preferably in a proportion of 2% to 10% by weight.

In particular, the composition according to the invention does not comprise 2% by weight, with respect to the total weight of the composition, of aminosilicone.

Furthermore, the composition according to the invention can comprise adjuvants commonly used in cosmetic compositions, in particular topical compositions. Mention may be made, by way of example of adjuvants, of dyes, pigments, pearlescent agents, UV-inhibiting agents, preservatives, thickening agents, plasticizing agents, surfactants, waxes, oils, fragrances, pH-modifying agents or moisturizing agents. Of course, a person skilled in the art will take care to choose this or these optional adjuvants and/or their amount so that the advantageous properties of the composition according to the invention are not, or not substantially, detrimentally affected by the envisaged addition.

The composition according to the invention can be used for nontherapeutically making up, caring for or cosmetically treating keratinous substances and/or mucous membranes. The make-up composition can be a product for making up the lips, in particular in the form of a paste or stick, a foundation, an eyeshadow, a face powder, a mascara for the eyelashes or hair, an eyeliner, a concealer or alternatively a composition for making up the body. The care or cosmetic treatment composition can be a composition for caring for the face, neck, hands, body, nails or lips, a deodorant composition or a sun protection composition.

The invention also relates to a non-therapeutic process for treating or making up keratinous substances and/or mucous membranes which comprises applying, to the keratinous substances and/or mucous membranes, a composition as described above.

Another subject-matter of the invention is the use of a terephthalic copolyester oligomer and of at least one silicone compound in aqueous emulsion as defined above in a cosmetic or dermatological composition for decreasing, indeed even virtually eliminating, the transfer of the film of this composition deposited on keratinous substances and/or mucous membranes and/or for virtually eliminating the deposition of traces on another substrate other than said keratinous substances and/or said mucous membranes.

Another subject-matter of the invention is the use of a terephthalic copolyester oligomer and of at least one silicone compound in aqueous emulsion as defined above in a cosmetic or dermatological composition for producing a film of this composition which is glossy and/or is fresh and/or is comfortable.

A further subject-matter of the invention is the use of a composition as defined above for producing a film of this composition which is glossy and/or is fresh and/or is comfortable and/or which has excellent transfer resistant properties.

Examples illustrating the present invention without, however, limiting it will now be given.

EXAMPLE 1

Preparation of a terephthalic copolyester oligomer

The following are introduced into a 7.5 liter reactor made of stainless steel which is equipped with an anchor stirrer rotating at 80 rev/min connected to a Kyowa torquemeter, with a jacket for the circulation of a heat-transfer liquid and with a distillation column regulated by an electrically-operated valve:

11.47 mol of dimethyl terephthalate 2.53 mol of sodium dimethyl isophthalate-5-sulfonate 39.16 mol of ethylene glycol 54 ppm by weight of titanium, in the form of titanium aminotriethanolate, as catalyst and etherification-limiting agent.

The mixture is preheated to 180° C. It is subsequently brought to a temperature of 220° C. over approximately 130 minutes, in order to distill off more than 90% of the theoretical amount of methanol.

The reaction mixture is subsequently brought to 230° C. over 30 minutes. When the reaction mass has reached this temperature, a suspension with the following composition:

0.5 mol of isophthalic acid 2.36 mol of terephthalic acid 8 mol of ethylene glycol is introduced over 60 minutes, still at 230° C.

The reaction mass is then brought to a temperature of 250° C. over 60 minutes. During the period of introduction of the mixture and during the period of heating to 250° C., a mixture of water and ethylene glycol is distilled off without retrogradation.

The reaction mixture is subsequently transferred to an autoclave preheated to 250° C. and then placed under a reduced pressure of 100 millibar over 22 minutes. After 2 minutes under these temperature and pressure conditions, the reaction mass is cast and cooled.

The copolyester obtained exhibits the structural characteristics described in Table 1 below, in which:

"Molar % of the diacid units" corresponds to the content in % of each diacid or diester employed with respect to the combined diacids or diesters employed.

"Tp" means: terephthalic unit

"Ip" means: isophthalic unit

"Slp" means: sulfoisophthalic unit

The characteristics of the "glycol" part of the copolyesters are obtained by methanolysis of the products at 190° C. for 16 hours, followed by analysis by the gas chromatography technique and quantitative determination by internal standardization.

"Molar % of the diol units" corresponds to the content in % of oxyethylene units "G", di(oxyethylene) units "2G", tri(oxyethylene) units "3G" and tetra(oxyethylene) units "4G" with respect to the combined diol units.

*"% GT/Σ units" corresponds to the molar % of the units of formula (I)

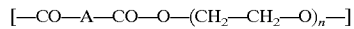

$$[-CO-A-CO-O-(CH_2-CH_2-O)_n-] \qquad (I)$$

where A is 1,4-phenylene and n=1 with respect to the combined units of formula (I) where A is 1,4-phenylene, sulfo-1,3-phenylene and optionally 1,3-phenylene and n ranges from 1 to 4

"% GT/Σ units" is calculated by the following formula:

% GT/Σ units=(molar % of Tp units)×(molar % of G units)/100

*The molar mass of the polyesters (Mw) is determined by gel permeation chromatography (GPC) in DMAc/LiBr at 100° C. and the results are given in polystyrene equivalents.

| Molar % of the diacid units | |
|---|---|
| Tp | 82 |
| Ip | 3 |
| Slp | 15 |
| % GT/Σ units | 46.5 |
| Molar % of the diol units | |
| G | 56.8 |
| 2G | 30.7 |
| 3G | 10 |
| 4G | 2.5 |
| Mw | 8000 |

EXAMPLE 2

A lipstick was prepared in the form of a stick having the following composition:

| | |
|---|---|
| terephthalic copolyester oligomer of Example 1 | 20% |
| alkylated polydimethylsiloxane emulsion with a solids content of 50% (Silres M50E from Wacker) | 5% AM |
| pigments | 5% |
| propylene glycol | 2.5% |
| water | q.s. for 100% |

A lipstick is obtained which is easy to apply and which makes it possible to obtain an excellent transfer-resistant film which is perfectly glossy.

EXAMPLE 3

A lipstick was prepared in the form of a stick having the following composition:

| | |
|---|---|
| terephthalic copolyester oligomer of Example 1 | 20% |
| aminated polydimethylsiloxane emulsion with a solids content of 35% (Belsil ADM 6057E from Wacker) | 10% AM |
| pigments | 5% |
| propylene glycol | 2.5% |
| water | q.s. for 100% |

A lipstick is obtained which makes it possible to obtain an excellent transfer-resistant film which is extremely glossy.

EXAMPLE 4

An eyeliner was prepared in the form of a gel having the following composition:

| | |
|---|---|
| terephthalic copolyester oligomer of Example 1 | 10% |
| phenylated polydimethylsiloxane emulsion with a | 4% AM |

| | |
|---|---|
| solids content of 50% (Mirasil DPDM-E from Rhône-Poulenc) | |
| black pigments | 3% |
| propylene glycol | 1.5% |
| water | q.s. for 100% |

An eyeliner is obtained which makes it possible to obtain an excellent transfer-resistant make-up which leaves a perfectly glossy film.

What is claimed is:

1. A film-forming, aqueous phase, topical application composition comprising
   i) a hydrophilic gelling agent chosen from water-soluble and water-dispersible terephthalic copolyester oligomers comprising dicarboxylate repeat units of formula (I):

$$[—CO—A—CO—O—(CH_2—CH_2O)_n—] \quad (I)$$

wherein
   A comprises 1,4-phenylene and sulfo-1,3-phenylene groups,
   n ranges from 1 to 4,
   at least 35 mol % of said units of formula (I) are units of formula (I), wherein A is a 1,4-phenylene group and n is equal to 1, and
   at least 7 mol % of the said units of formula (I) are units of formula (I), wherein A is a sulfo-1,3-phenylene group, and
   the weight-average molecular mass of said terephthalic copolyester oligomers is less than 20,000, and
   ii) at least one silicone compound as an aqueous phase emulsion, wherein said composition does not comprise 2% by weight, with respect to the total weight of the composition, of aminosilicone.

2. The composition according to claim 1, wherein said A further comprises a 1,3-phenylene group.

3. The composition according to claim 2, wherein said terephthalic copolyester oligomers comprise up to 20 mol % of said units of formula (I), wherein A is a 1,3-phenylene group.

4. The composition according to claim 2, wherein said terephthalic copolyester oligomers comprise from 0.5 mol % to 5 mol % of said units of formula (I), wherein A is a 1,3-phenylene group.

5. The composition according to claim 1, wherein said terephthalic copolyester oligomers have a weight-average molecular mass of less than 15,000.

6. The composition according to claim 1, wherein said terephthalic copolyester oligomers have a weight-average molecular mass ranging from 5000 to 14,000.

7. The composition according to claim 1, wherein said terephthalic copolyester oligomers have a weight-average molecular mass ranging from 8000 to 10,000.

8. The composition according to claim 1, wherein said terephthalic copolyester oligomers comprise at least 40 mol % of said units of formula (I), wherein said A is a 1,4-phenylene group and n is equal to 1.

9. The composition according to claim 8, wherein said terephthalic copolyester oligomers comprise from 40 to 90 mol % of said units of formula (I), wherein A is a 1,4-phenylene group and n is equal to 1.

10. The composition according to claim 1, wherein said terephthalic copolyester oligomers comprise at least 10 mol % of said units of formula (I), wherein said A is a sulfo-1,3-phenylene group.

11. The composition according to claim 10, wherein said terephthalic copolyester oligomers comprise from 10 mol % to 25 mol % of said units of formula (I), wherein said A is a sulfo-1,3-phenylene group.

12. The composition according to claim 1, wherein said terephthalic copolyester oligomers comprise up to 20 mol % of units of formula (I) in which A is a 1,3-phenylene group.

13. The composition according to claim 12, wherein said terephthalic copolyester oligomers comprise from 0.5 mol % to 5 mol % of units of formula (I) in which A is a 1,3-phenylene group.

14. The composition according to claim 1, wherein said hydrophilic gelling agent is present in an amount ranging from 0.5% to 40% by weight with respect to the total weight of the composition.

15. The composition according to claim 14, wherein said hydrophilic gelling agent is present in an amount ranging from 10% to 40% by weight with respect to the total weight of the composition.

16. The composition according to claim 14, wherein said hydrophilic gelling agent is present in an amount ranging from 15% to 30% by weight with respect to the total weight of the composition.

17. The composition according to claim 1, wherein said composition is in the form of a gel, and wherein said hydrophilic gelling agent is present in an amount ranging from 0.5% to 10% by weight with respect to the total weight of the composition.

18. The composition according to claim 17, wherein said composition is in the form of a gel, and wherein said hydrophilic gelling agent is present in an amount ranging from 2% to 5% by weight with respect to the total weight of the composition.

19. The composition according to claim 1, wherein said aqueous emulsion of said at least one silicone compound has a droplet size ranging from 10 nm to 50 µm.

20. The composition according to claim 19, wherein said aqueous emulsion of said at least one silicone compound has a droplet size ranging from 10 nm to 1000 nm.

21. The composition according to claim 1, wherein said at least one silicone compound is chosen from polyorganosiloxanes.

22. The composition according to claim 1, wherein said at least one silicone compound is chosen from silicone oils, gums, resins, pasty products and waxes.

23. The composition according to claim 1, wherein said at least one silicone compound is chosen from volatile and nonvolatile silicone oils.

24. The composition according to claim 1, wherein said at least one silicone compound is chosen from polyalkylsiloxanes, polyarylsiloxanes, polyalkylarylsiloxanes, polyethersiloxane copolymers, which may or may not be organomodified, and polysiloxanes modified by organofunctional groups.

25. The composition according to claim 1, wherein said at least one silicone compound is chosen from linear polydimethylsiloxanes with trimethylsilyl end groups; linear polydimethylsiloxanes with dimethylsilanol end groups; polydimethylmethylphenylsiloxanes; and polydimethyldiphenylsiloxanes.

26. The composition according to claim 1, wherein said at least one silicone compound is present in an amount on a dry basis ranging from 0.1% to 30% by weight with respect to the total weight of the composition.

27. The composition according to claim 26, wherein said at least one silicone compound is present in an amount on a dry basis ranging from 2% to 10% by weight with respect to the total weight of the composition.

28. The composition according to claim 1, wherein said composition is a cosmetic or dermatological composition.

29. The composition according to claim 1, wherein said composition further comprises at least one adjuvant chosen from dyes, pigments, pearlescent agents, UV-inhibiting agents, preservatives, thickening agents, plasticizing agents, surfactants, waxes, oils, fragrances, pH-modifying agents and moisturizing agents.

30. The composition according to claim 1, wherein said composition is in the form of a composition for making up, for caring for or for cosmetically treating a keratinous substance or a mucous membrane.

31. The composition according to claim 1, wherein said composition is a product for making up the lips, a foundation, an eyeshadow, a face powder, a mascara, an eyeliner, a concealer, a composition for making up the body, a composition for caring for the face, neck, hands, body, nails or lips, a deodorant composition or a sun protection composition.

32. A non-therapeutic process for making up or treating a keratinous substance or a mucous membrane, comprising applying to said keratinous substance or said mucous membrane an effective amount of a film-forming, aqueous phase composition comprising i) a hydrophilic gelling agent chosen from water-soluble and water-dispersible terephthalic copolyester oligomers comprising dicarboxylate repeat units of formula (I):

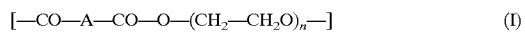

wherein
A comprises 1,4-phenylene and sulfo-1,3-phenylene groups,
n ranges from 1 to 4,
at least 35 mol % of said units of formula (I) are units of formula (I), wherein A is a 1,4-phenylene group and n is equal to 1, and
at least 7 mol % of the said units of formula (I) are units of formula (I), wherein A is a sulfo-1,3-phenylene group, and
the weight-average molecular mass of said terephthalic copolyester oligomers is less than 20,000, and ii) at least one silicone compound as an aqueous phase emulsion, wherein said composition does not comprise 2% by weight, with respect to the total weight of the composition, of aminosilicone.

33. A process for decreasing the transfer of a film of a topical application composition deposited on a keratinous substance or a mucous membrane or for eliminating the deposition of traces of said composition on another substrate other than said keratinous substance or said mucous membrane comprising including in a topical composition an effective amount of a film-forming, aqueous phase composition comprising i) a hydrophilic gelling agent chosen from water-soluble and water-dispersible terephthalic copolyester oligomers comprising dicarboxylate repeat units of formula (I):

wherein
A comprises 1,4-phenylene and sulfo-1,3-phenylene groups,
n ranges from 1 to 4,
at least 35 mol % of said units of formula (I) are units of formula (I), wherein A is a 1,4-phenylene group and n is equal to 1, and
at least 7 mol % of the said units of formula (I) are units of formula (I), wherein A is a sulfo-1,3-phenylene group, and
the weight-average molecular mass of said terephthalic copolyester oligomers is less than 20,000, and
ii) at least one silicone compound as an aqueous phase emulsion, wherein said composition does not comprise 2% by weight, with respect to the total weight of the composition, of aminosilicone.

34. A process of rendering a film of a cosmetic or dermatological composition glossy and/or fresh and/or comfortable comprising including in said composition an effective amount of a film-forming, aqueous phase composition comprising
i) a hydrophilic gelling agent chosen from water-soluble and water-dispersible terephthalic copolyester oligomers comprising dicarboxylate repeat units of formula (I):

$$[-CO-A-CO-O-(CH_2-CH_2O)_n-] \tag{I}$$

wherein
A comprises 1,4-phenylene and sulfo-1,3-phenylene groups,
n ranges from 1 to 4,
at least 35 mol % of said units of formula (I) are units of formula (I), wherein A is a 1,4-phenylene group and n is equal to 1, and
at least 7 mol % of the said units of formula (I) are units of formula (I),
wherein A is a sulfo-1,3-phenylene group, and
the weight-average molecular mass of said terephthalic copolyester oligomers is less than 20,000, and
ii) at least one silicone compound as an aqueous phase emulsion, wherein said composition does not comprise 2% by weight, with respect to the total weight of the composition, of aminosilicone.

35. A process for producing a film of a composition which is glossy, is fresh, is comfortable, or has non-transfer properties comprising the step of including in said composition an effective amount of a film-forming, aqueous phase composition comprising
i) a hydrophilic gelling agent chosen from water-soluble and water-dispersible terephthalic copolyester oligomers comprising dicarboxylate repeat units of formula (I):

$$[-CO-A-CO-O-(CH_2-CH_2O)_n-] \tag{I}$$

wherein
A comprises 1,4-phenylene and sulfo-1,3-phenylene groups,
n ranges from 1 to 4,
at least 35 mol % of said units of formula (I) are units of formula (I), wherein A is a 1,4-phenylene group and n is equal to 1, and
at least 7 mol % of the said units of formula (I) are units of formula (I),
wherein A is a sulfo-1,3-phenylene group, and
the weight-average molecular mass of said terephthalic copolyester oligomers is less than 20,000, and
ii) at least one silicone compound as an aqueous phase emulsion, wherein said composition does not comprise 2% by weight, with respect to the total weight of the composition, of aminosilicone.

* * * * *